(12) United States Patent
Katz et al.

(10) Patent No.: US 9,404,825 B2
(45) Date of Patent: Aug. 2, 2016

(54) APPARATUS WITH FLEXIBLE MEMBER FOR SENSING FLUID PRESSURE

(71) Applicant: Fenwal, Inc., Lake Zurich, IL (US)

(72) Inventors: Steven R. Katz, Deerfield, IL (US);
Salvatore Manzella, Barrington, IL (US); Terry Chung, Kildeer, IL (US); Greg Pieper, Waukegan, IL (US); Natalie Osterweil, Evanston, IL (US)

(73) Assignee: FENWAL, INC., Lake Zurich, IL (US)

( * ) Notice: Subject to any disclaimer, the term of this patent is extended or adjusted under 35 U.S.C. 154(b) by 797 days.

(21) Appl. No.: 13/658,256

(22) Filed: Oct. 23, 2012

(65) Prior Publication Data
US 2013/0150225 A1    Jun. 13, 2013

Related U.S. Application Data

(60) Provisional application No. 61/567,854, filed on Dec. 7, 2011.

(51) Int. Cl.
| | |
|---|---|
| *G01L 7/02* | (2006.01) |
| *G01L 9/14* | (2006.01) |
| *G01L 11/02* | (2006.01) |

(52) U.S. Cl.
CPC . *G01L 9/14* (2013.01); *G01L 11/02* (2013.01); *A61M 2205/12* (2013.01); *A61M 2205/3331* (2013.01)

(58) Field of Classification Search
None
See application file for complete search history.

(56) References Cited

U.S. PATENT DOCUMENTS

| | | | | |
|---|---|---|---|---|
| 5,086,777 A | * | 2/1992 | Hishii | A61B 5/0215 600/368 |
| 5,517,998 A | * | 5/1996 | Madison | A61B 5/03 600/473 |
| 5,644,285 A | * | 7/1997 | Maurer | G01L 9/0052 338/39 |
| 5,869,766 A | * | 2/1999 | Cucci | G01L 9/0075 73/706 |
| 6,764,460 B2 | | 7/2004 | Dolecek et al. | |
| 7,146,861 B1 | * | 12/2006 | Cook | A61B 5/0215 73/715 |
| 2002/0162397 A1 | * | 11/2002 | Orr | G01L 13/00 73/700 |
| 2005/0148884 A1 | * | 7/2005 | Parks | A61B 5/037 600/488 |
| 2006/0107749 A1 | * | 5/2006 | Liu | A61B 5/0002 73/754 |
| 2006/0117859 A1 | * | 6/2006 | Liu | A61B 5/02152 73/753 |
| 2007/0197922 A1 | * | 8/2007 | Bradley | A61M 39/08 600/488 |

FOREIGN PATENT DOCUMENTS

| | | | | |
|---|---|---|---|---|
| EP | 0768060 A1 | * | 4/1997 | ......... A61B 5/02158 |
| WO | WO 9739679 A1 | * | 10/1997 | ........... A61B 5/0215 |
| WO | WO 9847424 A1 | * | 10/1998 | ........... A61B 5/0215 |
| WO | WO 2007095597 A1 | * | 8/2007 | ............ A61M 39/08 |

* cited by examiner

*Primary Examiner* — Andre Allen
(74) *Attorney, Agent, or Firm* — Foley & Lardner LLP (57) ABSTRACT

One embodiment relates to a pressure sensor apparatus, including a housing with a flexible member and an aperture configured to receive a fluid. The pressure sensor apparatus further includes a first member disposed on the flexible member, a second member removeably coupled to the first member configured to move in response to a pressure of the fluid and a sensor configured to detect the movement of the second member. The pressure sensor apparatus generates a pressure signal for the fluid based on the displacement of the second member.

11 Claims, 9 Drawing Sheets

APPARATUS WITH FLEXIBLE MEMBER FOR SENSING FLUID PRESSURE

CROSS-REFERENCE TO RELATED APPLICATIONS

This application claims the benefit of U.S. Provisional Application No. 61/567,854, filed Dec. 7, 2011, which is incorporated by reference herein in its entirety.

BACKGROUND

The present invention relates generally to a pressure sensor for a fluid (e.g., a gas or liquid). A wide variety of mechanisms may be used to detect the pressure of a fluid, including a piezoelectric mechanism, a potentiometer, an electromagnetic mechanism, a capacitor, or a piezoresistive mechanism.

In some applications, a disposable pressure sensor may be utilized. For example, a pressure sensor may be utilized in a machine that handles blood, such as a centrifuge that separates blood into its various components (e.g., red blood cells, platelets, plasma, etc.).

BRIEF DESCRIPTION OF THE DRAWINGS

Features, aspects, and advantages of the present invention will become apparent from the following description, appended claims, and the accompanying exemplary embodiments shown in the drawings, which are briefly described below.

DETAILED DESCRIPTION OF EXEMPLARY EMBODIMENTS

It is to be understood that the following detailed description is exemplary and explanatory only, and is not restrictive of the invention as claimed.

It is useful to measure the pressure inside a disposable blood-handling assembly with a pressure sensor in order to determine whether or not there are occlusions in the flow either upstream or downstream from the pressure sensor. Further, during installation checks, the disposable assembly may be checked for leaks by applying a positive or negative pressure to portions of the disposable assembly. Because portions of the assembly are disposable, and are advantageously inexpensive, some types of pressure transducers embedded in the disposable assembly would be cost prohibitive. Additionally, any sensors in the disposable assembly would have to withstand sterilization, would have to be biologically compatible, and would have to provide safety isolation from the donor/patient (e.g., be electrically isolated). Therefore, noninvasive pressure measurements are typically performed by either measuring the pressure via a diaphragm in the disposable assembly coupled to a load cell or via insertion of an open tube, often separated by a sterility filter, directly into a pressure transducer.

According to an exemplary embodiment, a sensor apparatus monitors the displacement of the diaphragm with a non-contact measurement, for example, by the sensor being disposed so as not to physically contact the diaphragm or disposable assembly. The diaphragm may be coupled to a spring with a known spring constant. The spring coupled to the diaphragm allows a near-linear conversion of the linear displacement of the diaphragm to the pressure inside the disposable assembly. The magnitude of the linear displacement of the diaphragm in the pressure range between a positive pressure position and a negative pressure position is a factor of the spring constant of the spring. The spring constant can be compensated for in calibration of the sensor apparatus.

Figure 1:
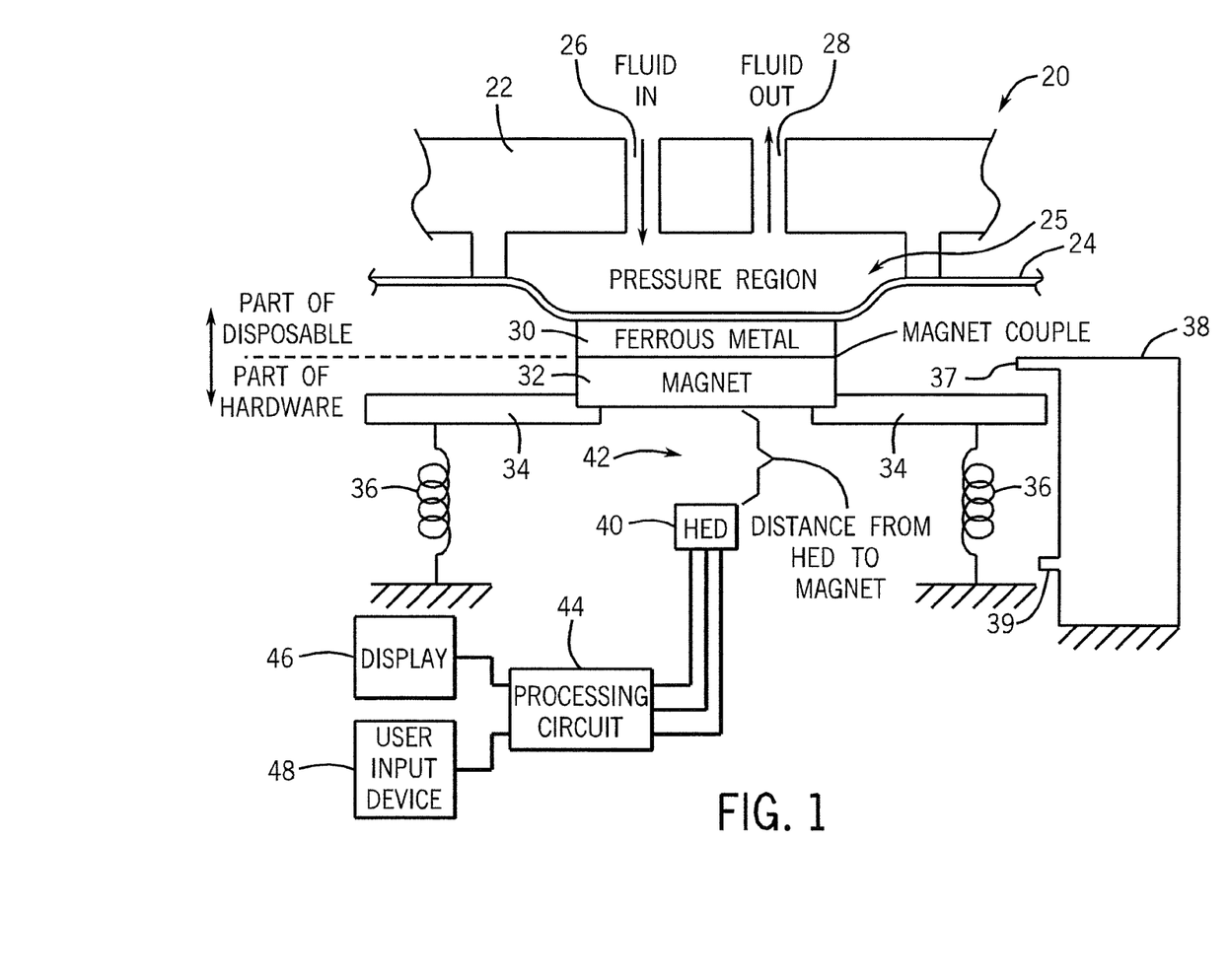
FIG. 1 is a side view of a pressure sensor in an initial or neutral state, according to an exemplary embodiment.
Figure 2:
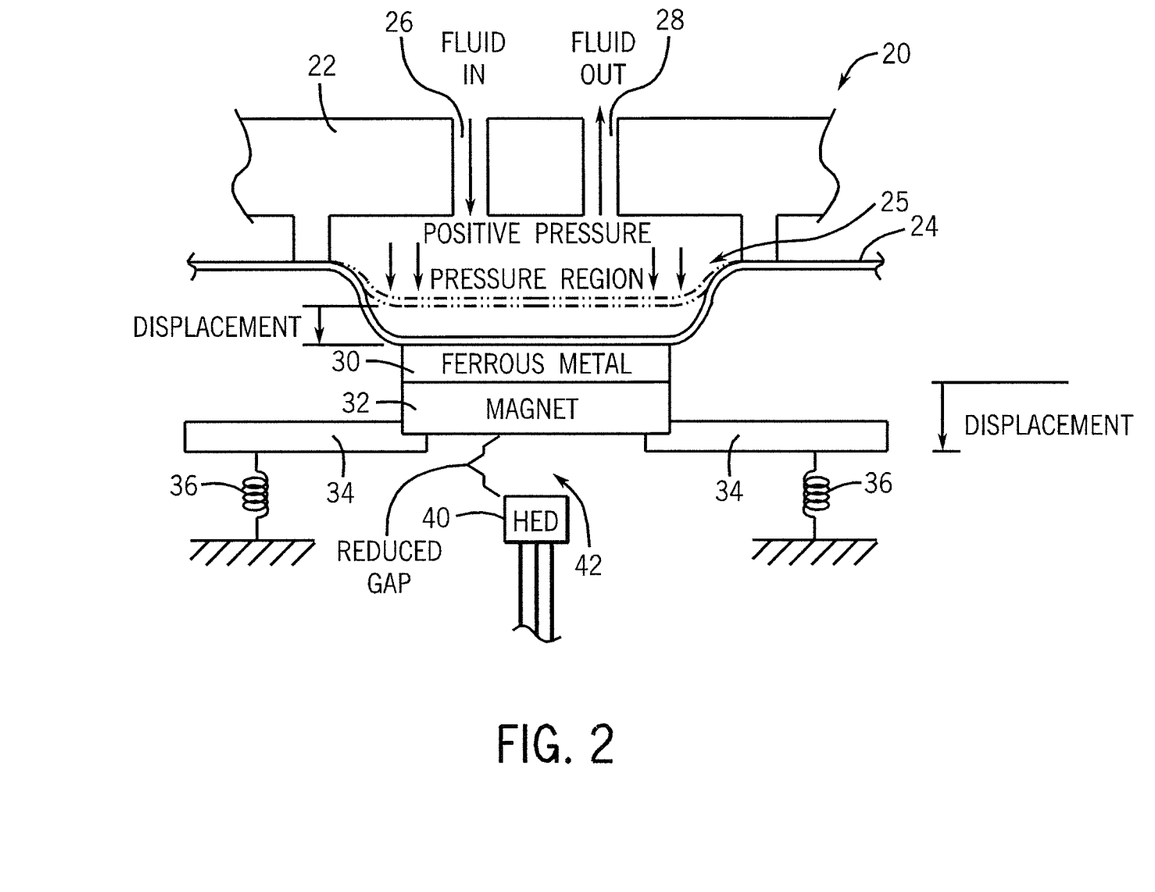
FIG. 2 is a side view of the pressure sensor of FIG. 1 in a positive pressure-sensing state, according to an exemplary embodiment.
Figure 3:
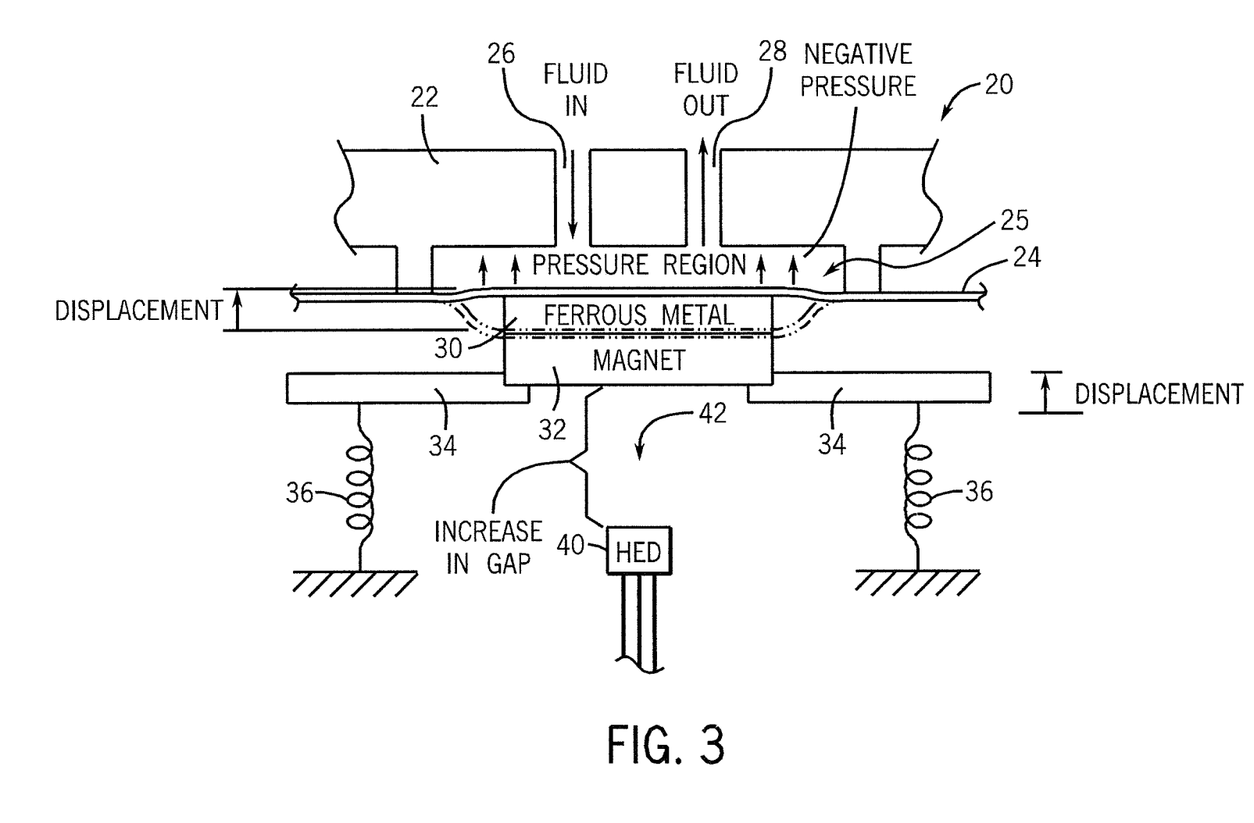
FIG. 3 is a side view of the pressure sensor of FIG. 1 in a negative pressure-sensing state, according to an exemplary embodiment.

Referring to FIGS. 1-3, one exemplary embodiment relates to a sensor apparatus 20 that may be utilized as a part of a larger system. The sensor apparatus 20 is configured to monitor the pressure of a fluid. Sensor apparatus 20 includes a generally hollow housing 22 with a flexible member 24. Housing 22 and flexible member 24 define an interior or chamber 25 to receive a fluid. The fluid may be contained in a fluid system 50 (see FIGS. 6-9). According to an exemplary embodiment, housing 22 includes an inlet 26 and an outlet 28 to allow fluid from fluid system 50 to enter and exit sensor chamber or pressure region 25. In other exemplary embodiments, housing 22 may include more than one inlet 26 or outlet 28, a single dual inlet/outlet, etc.

According to an exemplary embodiment, flexible member 24 (e.g., membrane, diaphragm, film, etc.) is formed from an elastomeric or other flexible material. Flexible member 24 can be a loose membrane that may or may not be coupled to housing 22, and may or may not be stretched tight. In an exemplary case in which flexible member 24 is not stretched tight, the flexible member does not stretch as it is displaced by the positive or negative pressure of the fluid and therefore the physical properties of the membrane can be largely ignored when calculating the pressure. The material chosen, the tightness of the material, and the amount of displacement may be chosen to remove the force required to stretch the membrane from the membrane movement equation. For example, silicone or PVC may be used, though silicone may be preferred in some embodiments because it can stretch farther without plastic deformation and has a lower Young's modulus than PVC.

Flexible member 24 is configured to move in response to a pressure of the fluid admitted into chamber 25 through inlet 26. Pressure exerted on flexible member 24 forces flexible member 24 to deform relative to a base or no-load configuration in which an equal pressure is being exerted on both sides of flexible member 24 (e.g., atmospheric pressure outside of sensor apparatus 20 and in chamber 25), as shown in FIG. 1. If the pressure in chamber 25 is greater than atmospheric pressure (e.g., a positive pressure in fluid system 50), flexible member 24 is deformed away from chamber 25, as shown in FIG. 2. If the pressure in chamber 25 is less than atmospheric pressure (e.g., a vacuum or negative pressure in fluid system 50), flexible member 24 is deformed into chamber 25, as shown in FIG. 3. The magnitude of the pressure in fluid system 50 (e.g., the pressure differential between chamber 25 and atmospheric pressure) is proportional or otherwise related to the relative deformation or displacement of flexible member 24.

Sensor apparatus 20 further may include a rigid or movable member 30 coupled to the outer surface of flexible member 24. According to an exemplary embodiment, rigid member 30 is a disk formed of a ferrous metal. Rigid member 30 may, for example, be coupled to flexible member 24 with a permanent adhesive, vacuum coupling, or other coupling mechanism. In other exemplary embodiments, flexible member 24 may be replaced with a relatively rigid device, such as a shuttle, rigid capsule, or a ball bearing that is confined, for example, by a track or tube in fluid communication with chamber 25 and the exterior atmosphere. A rigid movable member may be configured to move back and forth along the track or tube in response to a pressure differential between chamber 25 and atmospheric pressure. In alternative embodiments, rigid member 30 may be molded to, integral with, or otherwise move with flexible member 24.

In an alternative embodiment, rigid member 30 may be omitted or replaced with a second flexible member. In one example, the flexible member 24 and/or second flexible member may be embedded with or otherwise comprise iron particles if the coupling is magnetic. Alternatively, in the case of a vacuum coupling, there could be no member intermediate the flexible member and a portion of the remainder of the system. According to another embodiment, flexible material 24 may comprise ferrous or magnetic particles such that the distance to sensor 40 can be detected directly without requiring rigid member 30 or magnet 32.

Rigid member 30 provides a mechanism with which a disposable portion of sensor apparatus 20 that directly interfaces with the fluid (e.g., housing 22, and flexible member 24) may be coupled to a relatively permanent portion attached to, for example, a centrifuge system described below. According to an exemplary embodiment, rigid member 30 is coupled to a magnet 32 with a magnetic force. The coupling between rigid member 30 and magnet 32 is configured to be temporary, allowing the disposable portion of sensor apparatus 20 to be easily removed from the more permanent portion of sensor apparatus 20. According to other exemplary embodiments, the magnet may be coupled to rigid member 30 with another removable coupling mechanism (e.g., an adhesive, a vacuum, a physical catch, Velcro, a high-friction surface of a material, an elastomeric material, etc.). The coupling of rigid member 30 and magnet 32 allows for both positive and negative pressures to be measured via positive and negative displacement of the interconnected flexible member 24, rigid member 30, and magnet 32. The coupling also allows for removability by force of a person's hand, or without the need for a tool.

The movement of magnet 32 is constrained by one or more biasing elements such as springs 36 and a magnet housing 38. Housing 38 may include mechanical stops, protrusions, or extensions 37 and 39. As shown in FIG. 1, stops 37 and 39 may extend inward from the main body of housing 38 and may be configured to limit the travel of magnet 32 as flexible member 24 is deformed. Stops 37 and 39 may not directly contact magnet 32, but may instead contact an intermediate body, such as a carrier 34. For instance, if magnet 32 is a disk-shaped body, carrier 34 may be a generally annular body surrounding magnet 32. Stops 37 and 39 provide overload protection for both excessive positive pressures (stop 39) and negative pressures (stop 37). Limiting the travel of magnet 32 and carrier 34 may advantageously prevent magnet 32 or carrier 34 from contacting sensor 40 and damaging magnet 32 and/or sensor 40.

Springs 36 bias magnet 32 towards a neutral position, shown in FIG. 1, and provide a force resisting displacement of magnet 32 in either the positive or negative directions. Springs 36 are coupled on one end to magnet 32 and on the opposite end to a non-movable body, such as housing 38. According to an exemplary embodiment, springs 36 are not coupled directly to magnet 32, but instead to carrier 34. The magnitude of the displacement of magnet 32 by a known fluid pressure acting on flexible member 24 is determined at least partially by the spring constant of springs 36. Springs 36 may be configured with a relatively high spring constant such that there is a relatively small displacement of magnet 32 between positive fluid pressures as shown in FIG. 2 and negative fluid pressures, as shown in FIG. 3.

The introduction of the spring to balance the rigid member against the force from the fluid pressure allows the system to use a flexible member that provides little resistance to movement—for example, silicone—such that the spring force is many times greater than the resistive force of the flexible member. Therefore, the spring provides a linear and controlled response to the force of the pressurized fluid ($F=-kx$; where k is the spring constant and x is the displacement). Thus, in one embodiment, displacement of the combination flexible member and rigid member is directly proportional to the pressure of the fluid and only varies based on the spring constant, which is constant over a wide range of conditions over time.

The displacement of magnet 32 is detected and monitored by a sensor 40. Sensor 40 transmits a signal to be analyzed by a computer or other device to detect changes in position of magnet 32 (e.g., deflection, translation, etc.) and to calculate or determine the pressure of fluid system 50 based on the detected or measured position changes. Sensor 40 is positioned such that it is separated from magnet 32 by a gap 42 and does not contact magnet 32. Magnet 32 is isolated by springs 36 and rigid member 30 coupled to flexible member 24. Therefore, the forces acting upon magnet 32 in this exemplary embodiment are the pressure acting on flexible member 24 and the reaction forces of springs 36. Because the displacement of magnet 32 may be small due to small magnitude fluid pressures in system 50 or springs 36 with high spring constants, sensor 40 may be a high resolution sensor.

According to an exemplary embodiment, sensor 40 may be a Hall Effect sensor that outputs a voltage that varies with the magnetic field acting on sensor 40. As shown in FIGS. 1-3, sensor 40 is provided at a distance from magnet 32 in line with magnet 32. A positive pressure in system 50 forces magnet 32 towards sensor 40, reducing gap 42 between magnet 32 and sensor 40 and increasing the magnetic field detected by sensor 40. A negative pressure in system 50 forces magnet 32 away from sensor 40, increasing gap 42 between magnet 32 and sensor 40 and decreasing the magnetic field detected by sensor 40. Magnet 32 therefore provides both a coupling mechanism between the disposable portions of sensor apparatus 20 and the non-disposable portions of sensor apparatus 20 and provides a means for detecting the displacement of flexible member 24. Alternative structures to magnet 32 may be used to provide either or both of these functions.

Hall Effect sensors can be less expensive than other commonly used sensors, such as a contact load cell. The resolution of Hall Effect sensors can be very high with a relatively small air gap 42 between magnet 32 and sensor 40. Therefore, very small movements of the interconnected flexible member 24, rigid member 30, and magnet 32 can be detected, allowing relatively high resolution conversion of displacement to pressure. In one example, a Honeywell SS490 series Miniature Ratiometric Linear Hall Effect integrated circuit chip may be used. The sensor may have a ratiometric output voltage, set by a supply voltage, that varies linearly in proportion to the strength of the magnetic field.

Figure 11:
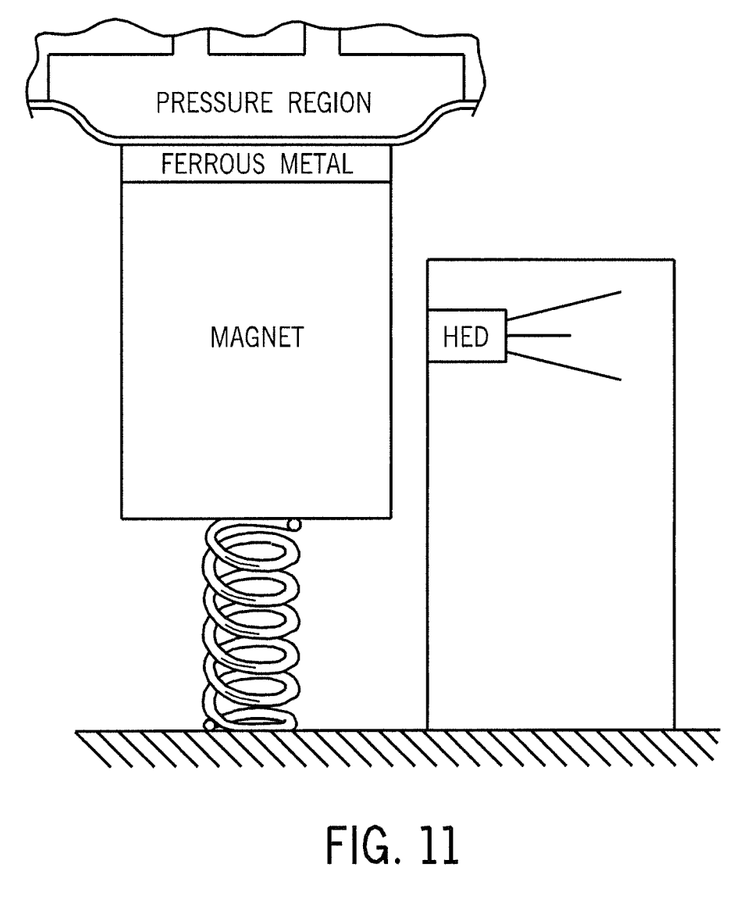
FIG. 11 is a side view of a pressure sensor, according to another alternative embodiment.

Referring to FIG. 11, in another alternative embodiment, a Hall Effect sensor may be positioned to the side rather than below the magnet such that the air gap is constant and the magnet moves parallel to the sensor. For a Hall Effect sensor, the change in magnetic field strength changes very linearly in proportion to the position in the middle portion (e.g., ~30%) of the magnet, whereas in the embodiments of FIGS. 1-3, the magnetic field strength is logarithmically proportional to the air gap distance.

Figure 4:
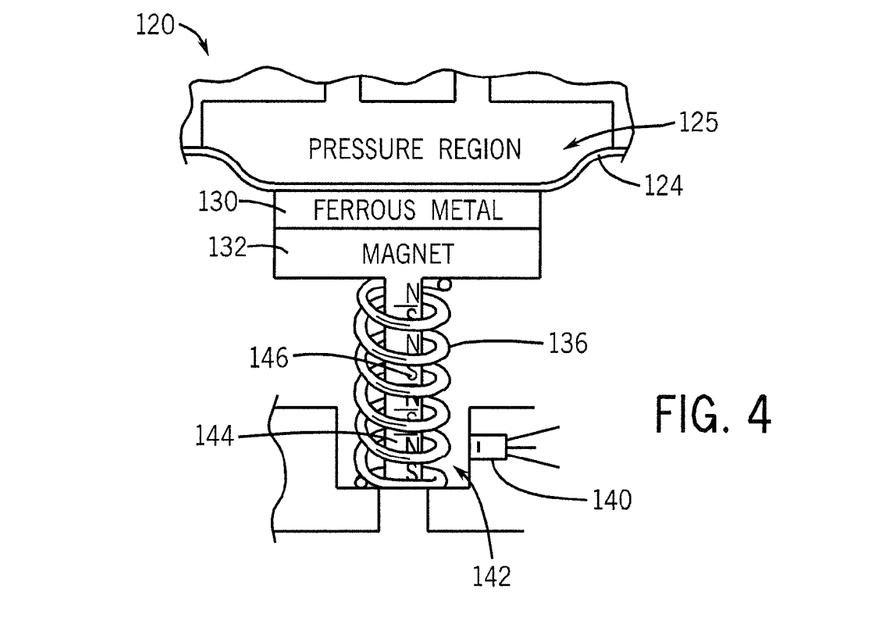
FIG. 4 is a side view of a pressure sensor in an initial or neutral state, according to an exemplary embodiment.

Referring to FIG. 4, a sensor apparatus 120 is shown according to another exemplary embodiment. Sensor apparatus 120 is similar to sensor apparatus 20, with an interconnected flexible member 124, rigid member 130, and magnet 132 that are displaced by a fluid pressure in a chamber 125. However, in this embodiment magnet 132 includes a post 144 that extends outward opposite of rigid member 130. A magnetic strip 146 with alternating north and south poles is provided along post 144. The displacement of magnet 132 is resisted by a spring 136.

Sensor 140 is located proximate to post 144. Unlike sensor 40, sensor 140 is provided along the side of magnet 132 and the gap 142 between sensor 140 and magnet 132 does not substantially change as magnet 132 is displaced by a positive or negative pressure in system 50. Sensor 140 detects the displacement of magnet 132 by sensing the alternating magnetic fields of strip 146. Sensor 140 converts the switching of N-S poles caused by the movement of magnet 132 into incremental position change data. According to one exemplary embodiment, sensor 140 may be an AS5311 integrated linear Hall encoder, as marketed by austriamicrosystems AG of Styria, Austria.

Because sensor 140 does not directly sense the magnetic fields of magnet 132, but rather senses magnetic strip 146, according to other exemplary embodiments, the positions of magnet 132 and rigid member 130 may be reversed. Therefore, magnet 132 may be coupled directly to flexible member 124 and post 144 with magnetic strip 146 may extend from member 130. A magnetic couple is still formed between magnet 132 and member 130 and sensor 140 is able to detect the displacement of magnetic strip 146. In other embodiments, there could be no magnet 132 and the coupling of magnetic strip 146 to rigid member 130 or directly to flexible member 124 could be accomplished in other ways.

Figures 5A, 5B:
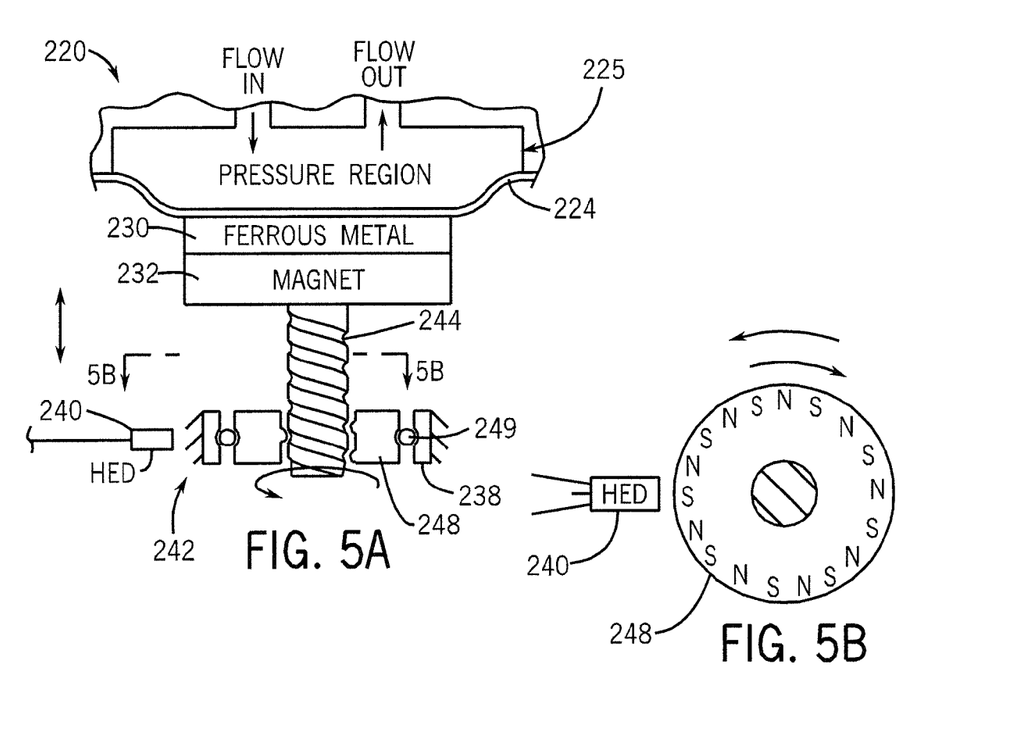
FIGS. 5A and 5B is a side view of a pressure sensor in an initial or neutral state, according to an exemplary embodiment.

Referring to FIG. 5, a sensor apparatus 220 is shown according to another exemplary embodiment. Sensor apparatus 220 is similar to sensor apparatus 120, with an interconnected flexible member 224, rigid member 230, and magnet 232 that are displaced by a fluid pressure in a chamber 225. However, post 244 extending from magnet 232 is a threaded member that engages a similarly threaded rotary member 248. Rotary member 248 is supported by a housing or frame 238. A support or bearing mechanism 249, for example ball bearings, may be provided between frame 238 and rotary member 248 to support rotational movement. Rotary member 248 is magnetic and is configured with alternating north and south poles about its periphery. A displacement of magnet 232 causes a rotation of rotary member 248 by the pitch of the threaded connection between post 244 and rotary member 248.

Sensor 240 is provided on a side of rotary member 248 and the gap 242 between sensor 240 and rotary member 248 does not change as rotary member 248 is rotated by a positive or negative pressure in system 50. Sensor 240 detects the displacement of magnet 232 by sensing the alternating magnetic fields about the periphery of rotary member 248. Sensor 240 converts the switching of N-S poles into incremental position changes. According to one exemplary embodiment, sensor 240 may be an AS5311 integrated linear Hall encoder, as marketed by austriamicrosystems of Styria, Austria.

Because sensor 240 does not directly sense the magnetic fields of magnet 232, according to other exemplary embodiments, the positions of magnet 232 and rigid member 230 may be reversed. Therefore, magnet 232 may be coupled directly to flexible member 224 and threaded post 244 may extend from member 230. A magnetic couple is still formed between magnet 232 and member 230 and sensor 240 is able to detect the displacement of rotary member 248 as it is rotated by the threaded connection to post 244.

As shown in FIG. 1, sensor 40 of sensor apparatus 20 may be coupled to a processing circuit 44. Processing circuit 44 is configured to calculate the pressure of fluid system 50 based on signals received from sensor 40. Processing circuit 44 may further be coupled to a display 46 to output the calculated pressure readings to a user. A user input device 48 may be provided to allow a user to interact with sensor apparatus 20 (e.g., by performing diagnostic tests, establishing a reference or zero condition, changing pressure units, resetting the device, etc.). Sensors 140 and 240 may be coupled to similar processing circuits.

Figure 6:
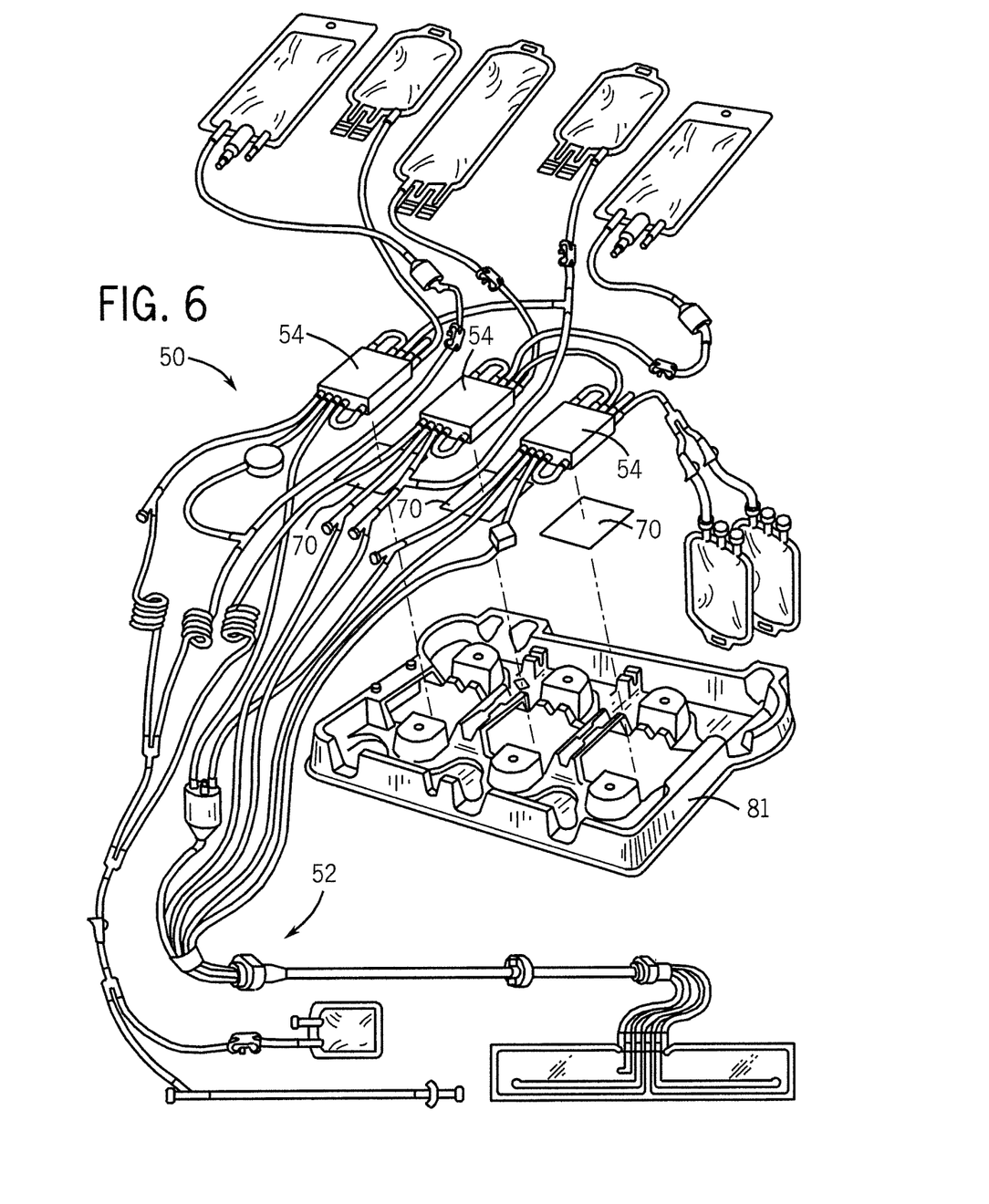
FIG. 6 is an exploded view of a disposable fluid processing assembly usable in association with a centrifuge assembly.

Referring now to FIG. 6, according to one exemplary embodiment, fluid system 50 may be utilized in a blood processing system to process whole blood or other suspensions of biological material. To avoid cross-contamination between donors, the blood processing system may include a first portion or housing configured to be reused for multiple blood processing operations for different donors, and a second portion or housing configured for a single blood processing operation. According to one exemplary embodiment, the first portion may be a device such as a centrifuge and the second portion may be a disposable fluid system 50 (e.g., a fluid processing assembly). Fluid system 50 is insertable to and removable from the centrifuge. Fluid system 50 includes conduits 52 configured to convey fluid through fluid system to and from the centrifuge or other mechanism. Fluid system 50 further includes one or more cassettes 54 that direct liquid flow among multiple fluid sources and destinations during a fluid processing procedure. A flexible membrane or diaphragm 70 is disposed in the cassettes 54. As described above, diaphragm 70 is configured to move in response to a change in pressure of the blood in fluid system 50. Fluid system 50 comprises a tray 81 which snaps over a cassette holder 80 (see FIG. 9).

Figure 7:
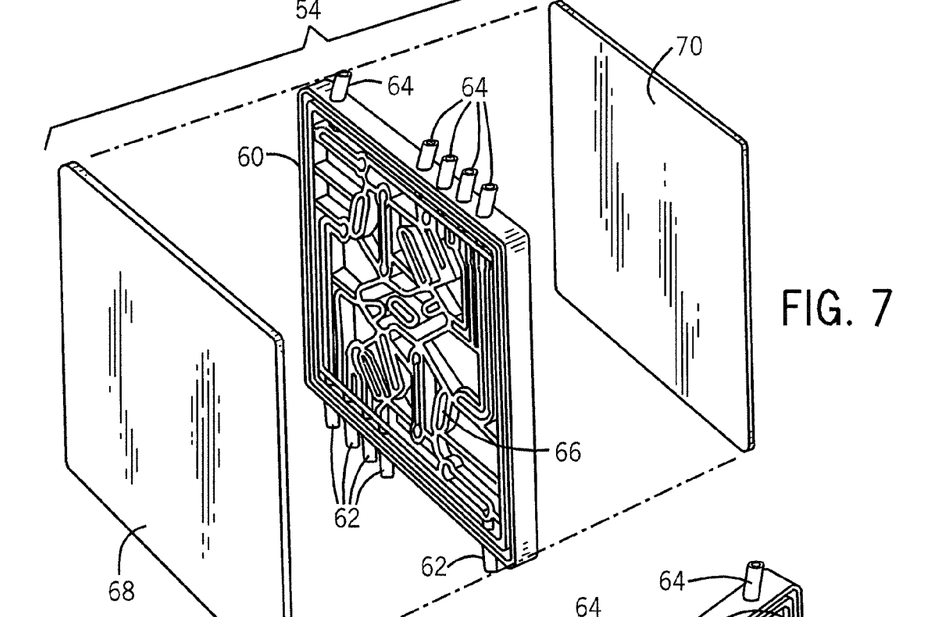
FIG. 7 is a rear isometric exploded view of a fluid control cassette that may be incorporated by the fluid processing assembly of FIG. 6.
Figure 8:
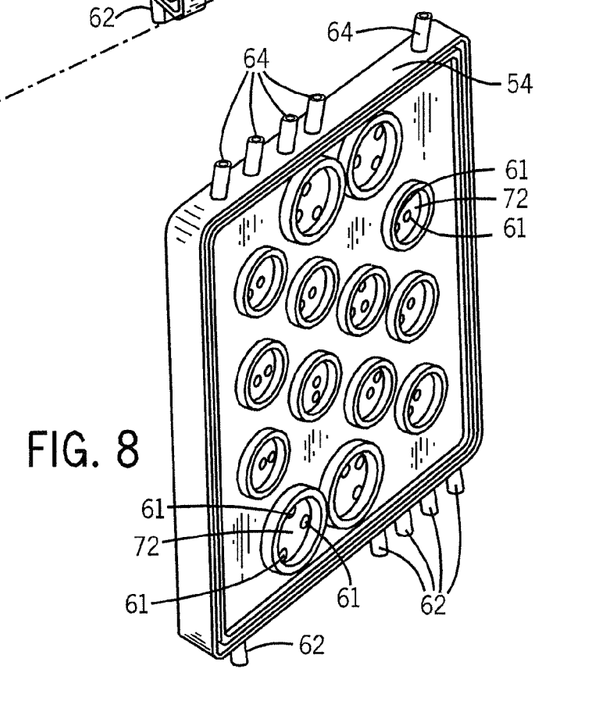
FIG. 8 is a front isometric view of the fluid control cassette of FIG. 7.

As shown in more detail in FIGS. 7 and 8, cassettes 54 have a body or housing 60 that is formed to include one or more input ports 62, one or more output ports 64, and channels 66 that direct fluid from inputs 62 to outputs 64. A cover or panel 68 is coupled to one side of housing 60 while flexible diaphragm 70 is coupled to the opposite side of housing 60.

Housing 60 further forms one or more open-ended sensing portions 72. Sensing portions 72 are analogous to chamber 25 of sensor apparatus 20 described above. Apertures 61 in housing 60 allow sensing portions 72 to be in fluid communication with channels 66. The open end of each sensing portion 72 is sealed by diaphragm 70 (e.g., with an ultrasonic welding operation, a vacuum, etc.). In this way, diaphragm 70 serves the same function as flexible member 24 of sensor apparatus 20 described above.

Figure 9:
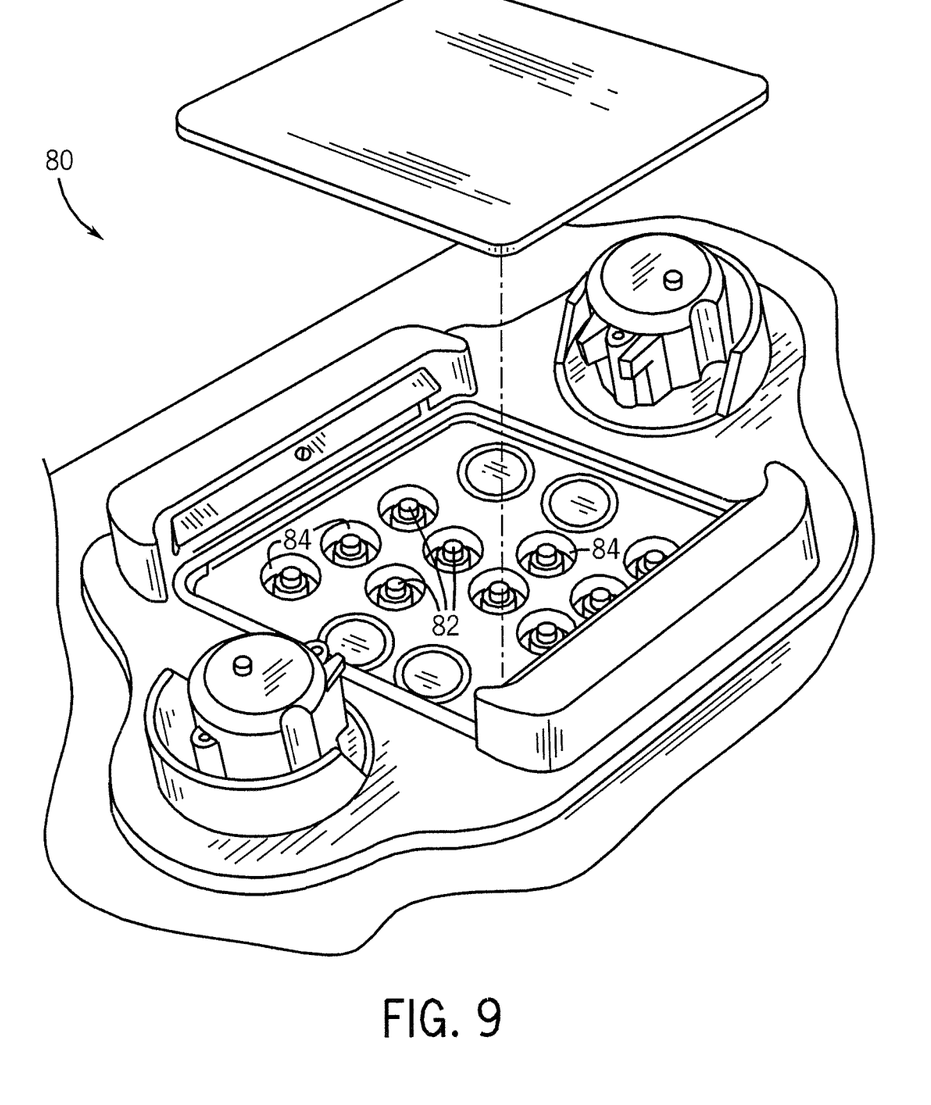
FIG. 9 is an isometric view of a cassette holding station for a centrifuge, according to an exemplary embodiment.

Referring now to FIG. 9, each cassette 54 is received in a holder 80 in the centrifuge. Holder 80 may include actuators 82 that interact with aligned valves in cassettes 54 to sense the displacement of diaphragm 70 proximate to sensing portions 72. Sensors may be provided adjacent to chambers 84 (e.g., hollows, recesses, cavities, etc.) formed in holder 80 that are aligned with sensing portions 72 of cassette 54. Holder 80 may therefore be analogous to magnet housing 38 of sensor apparatus 20 described above.

Once cassette 54 is inserted into holder 80, the sensor may detect the position of diaphragm 70 to establish a reference or zero condition. As a fluid such as blood flows through channels 66 in cassette 54, the displacement of portions of diaphragm 70 are monitored. The sensor may then generate a signal indicative of the movement and transmit the signal to a processing circuit configured to calculate a pressure of the blood in various channels 66. This data may be used for various other processes associated with the blood processing system, such as operating valves in cassettes 54 using actuators.

Figure 10:
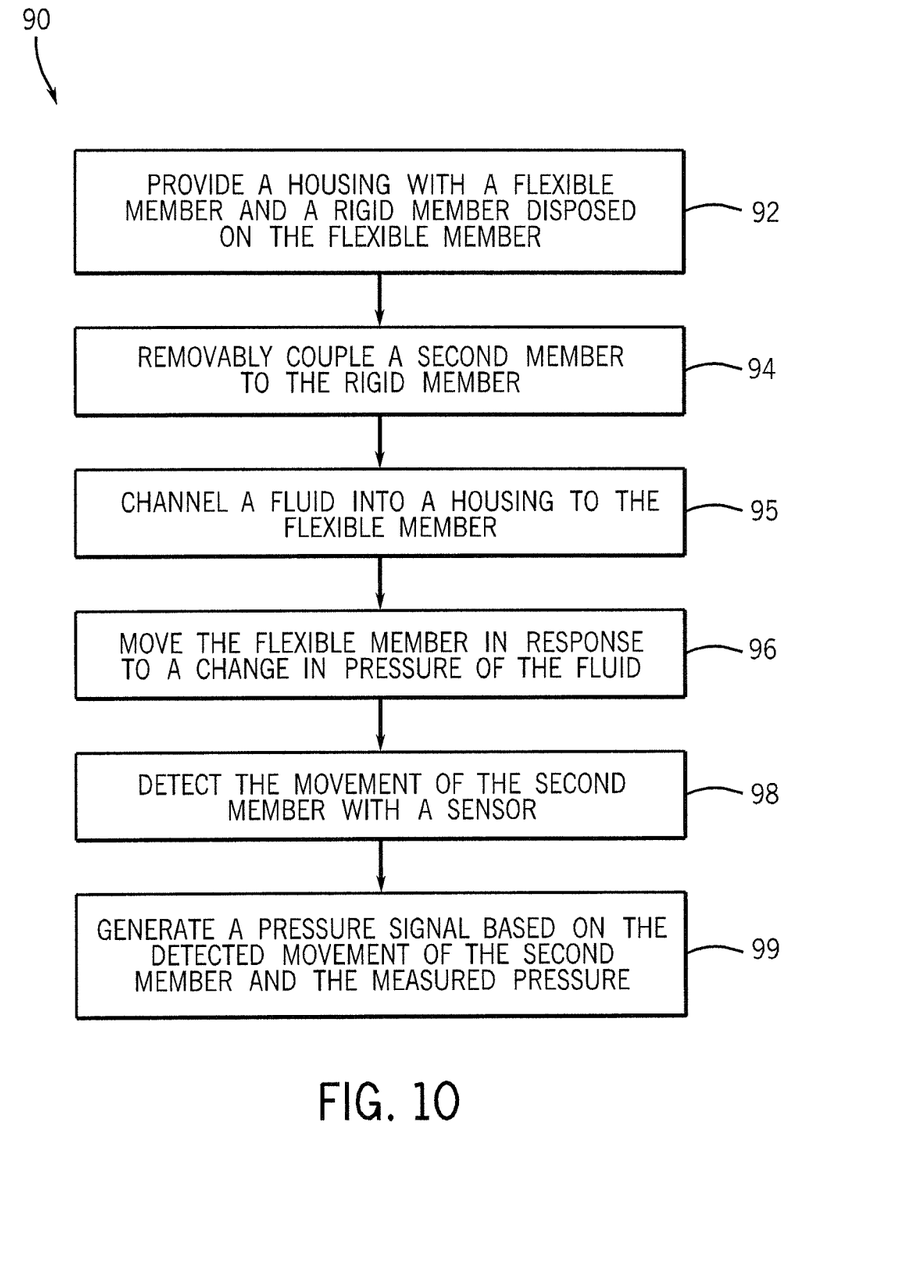
FIG. 10 is a flowchart of a method for measuring the pressure of a fluid, according to an exemplary embodiment.

Referring to FIG. 10, a flowchart of a method 90 for measuring the pressure of a fluid is shown according to an exemplary embodiment. A housing with a flexible member is first provided. A rigid member is disposed on the flexible member (step 92). A second member is then removeably coupled to the rigid member (step 94). A fluid is channeled into the housing to the flexible member (step 95). The flexible member is displaced or deformed in response to a change in pressure of the fluid (step 96). The flexible member may be moved in a first direction in response to an increase in pressure in the fluid and moved in a second direction opposite the first direction in response to a decrease in pressure of the fluid. The displacement or deformation of the second member is detected with a sensor (step 98). The second member may be, for example, magnetic, and the displacement of the second member may be detected with a magnetic field sensor. A pressure signal may be generated based on the detected movement of the second member (step 99).

Some embodiments may provide for noninvasive, extracorporeal pressure monitoring of a fluid, such as blood. Monitored pressure data may be utilized to facilitate the processing of the fluid, such as the separation of blood into its component parts.

Some embodiments may provide a low cost pressure sensor for systems in which some of the system is configured to be disposable. As described, sensor apparatus 20 is configured to include a portion interacting with the fluid (e.g., housing 22 and flexible member 24) that is relatively low cost that separates from a second portion that includes more expensive components (e.g., sensor 40). The lower cost components may then be disposed of after each use while the more expensive components are retained to be used multiple times.

Some embodiments may provide a pressure sensor with a disposable portion and a non-disposable portion that are coupled together with a temporary, removable coupling mechanism. In this way, the installation of a new disposable portion may be accomplished quickly and easily without negatively effecting the accuracy of data collected with the pressure sensor.

While the sensor apparatus has been described as utilizing magnetic field sensors to detect the displacement of a magnetic member coupled to the flexible membrane, in other embodiments, other sensors may be utilized. Such sensors may be non-contact sensors or may be contact sensors. For instance, displacement of the flexible membrane or members coupled to the flexible membrane may be detected with optical sensors, eddy current sensors, laser triangulation sensors, LVDT (linear variable differential transformer) sensors, potentiometers, etc. In one embodiment, an optical linear encoder may be used. An optical linear encoder may comprise an optical sensor, transducer or readhead paired with a scale that encodes position. The sensor reads the scale in order to convert the encoded position into an analog or digital signal, which can then be decoded into position by a digital controller. In place of N/S magnets as the scale, in this embodiment a clear or reflective strip of material with surface coatings or etchings creating a Ronchi or diffraction grating may be used as the scale, such that position can be ascertained by optically tracking or reading the movement from one gap to the next. Linear encoders other than optical linear encoders (e.g., magnetic linear encoders, etc.) may alternatively be used.

The construction and arrangement of the elements of the pressure sensor as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. Some like components have been described in the present disclosure using the same reference numerals in different figures (e.g., housing 22). This should not be construed as an implication that these components are identical in all embodiments; various modifications may be made in various different embodiments. It should be noted that the elements and/or assemblies of the enclosure may be constructed from any of a wide variety of materials that provide sufficient strength or durability, in any of a wide variety of colors, textures, and combinations. The processing circuit may comprise any digital and/or analog circuit components configured to perform the functions recited herein. The processing circuit may comprise one or more modules, units, circuits, etc., may comprise a microprocessor, microcontroller, application-specific integrated circuit, programmable logic, or other circuitry. The processing circuit may comprise a tangible computer-readable memory having instructions encoded thereon which when processed by a processor perform the functions recited herein. Additionally, in the subject description, the word "exemplary" is used to mean serving as an example, instance or illustration. Any embodiment or design described herein as "exemplary" is not necessarily to be construed as preferred or advantageous over other embodiments or designs. Rather, use of the word exemplary is intended to present concepts in a concrete manner. Accordingly, all such modifications are intended to be included within the scope of the present inventions. Other substitutions, modifications, changes, and omissions may be made in the design, operating conditions, and arrangement of the preferred and other exemplary embodiments without departing from the spirit of the appended claims.

What is claimed is:

1. A pressure sensor apparatus, comprising:
   a housing, comprising:
   a flexible member, and
   an aperture configured to receive a fluid, the flexible member configured to move in response to a change in pressure of the fluid;

a second member removeably coupled to the flexible member and configured to move together with the flexible member; and a sensor configured to sense a movement of the second member, the sensor separated from the second member by an air gap and configured to sense the movement of the second member across the air gap;

wherein the pressure sensor apparatus generates a pressure signal for the fluid based on the movement of the second member.

2. The pressure sensor apparatus of claim 1, wherein the flexible member is coupled to the second member with a vacuum coupling.

3. The pressure sensor apparatus of claim 1, further comprising a rigid member disposed on the flexible member, the second member removeably coupled to the rigid member.

4. The pressure sensor apparatus of claim 3, wherein the rigid member comprises a ferrous metal.

5. The pressure sensor apparatus of claim 4, wherein the second member is magnetically coupled to the rigid member.

6. The pressure sensor apparatus of claim 1, wherein the sensor does not contact the second member.

7. The pressure sensor apparatus of claim 6, wherein the sensor comprises a magnetic field sensor.

8. The pressure sensor apparatus of claim 7, wherein the sensor comprises an optical sensor.

9. The pressure sensor apparatus of claim 1, further comprising a third member, wherein the second member is threadably coupled to the third member.

10. The pressure sensor apparatus of claim 9, wherein the sensor detects a linear movement of the second member via a rotational movement of the third member.

11. The pressure sensor apparatus of claim 1, further comprising a spring coupled to a second housing configured to bias the second member toward the flexible member against the force of the pressure of the fluid.

* * * * *